United States Patent
Huff et al.

(10) Patent No.: US 12,156,801 B2
(45) Date of Patent: Dec. 3, 2024

(54) METHOD, APPARATUS, AND SYSTEM FOR BALANCING A PATIENT'S KNEE JOINT DURING AN ORTHOPAEDIC SURGICAL PROCEDURE

(71) Applicant: DePuy Ireland Unlimited Company, Ringaskiddy (IE)

(72) Inventors: Daniel N. Huff, Warsaw, IN (US); Kaela A. Wong, Warsaw, IN (US)

(73) Assignee: DEPUY IRELAND UNLIMITED COMPANY, Ringaskiddy (IE)

( * ) Notice: Subject to any disclaimer, the term of this patent is extended or adjusted under 35 U.S.C. 154(b) by 1100 days.

(21) Appl. No.: 17/039,904

(22) Filed: Sep. 30, 2020

(65) Prior Publication Data

US 2022/0096222 A1  Mar. 31, 2022

(51) Int. Cl.
| A61B 5/053 | (2021.01) |
| A61B 5/00 | (2006.01) |
| A61B 90/00 | (2016.01) |
| A61F 2/08 | (2006.01) |
| A61F 2/46 | (2006.01) |

(52) U.S. Cl.
CPC ............ *A61F 2/0805* (2013.01); *A61B 5/053* (2013.01); *A61B 5/4533* (2013.01); *A61B 5/6867* (2013.01); *A61B 5/742* (2013.01); *A61B 5/743* (2013.01); *A61B 90/06* (2016.02); *A61B 2090/064* (2016.02); *A61B 2505/05* (2013.01); *A61F 2002/0852* (2013.01); *A61F 2002/0864* (2013.01); *A61F 2002/4666* (2013.01)

(58) Field of Classification Search
CPC ....... A61F 2/0805; A61B 90/06; A61B 5/053; A61B 5/4533; A61B 5/743
See application file for complete search history.

(56) References Cited

U.S. PATENT DOCUMENTS

| 4,813,435 A | 3/1989 | Arms |
| 5,777,467 A | 7/1998 | Arms et al. |
| 8,211,041 B2* | 7/2012 | Fisher .................... A61B 17/88 |
| | | 600/595 |
| 9,364,169 B2 | 6/2016 | West et al. |
| 2013/0211279 A1* | 8/2013 | West .................... A61B 5/4533 |
| | | 600/547 |
| 2019/0209079 A1 | 7/2019 | Delport |

FOREIGN PATENT DOCUMENTS

| EP | 2166940 B1 | 2/2012 |
| WO | 2008148822 A1 | 12/2008 |

OTHER PUBLICATIONS

Kuo, J. et al., "Effect of Mechanical Loading on Electrical Conductivity in Porcine TMJ Discs," Journal of Dental Research, vol. 90, Issue 10, Oct. 2011, 5 pages.
International Search Report and Written Opinion for Application No. PCT/EP2021/077027, Jan. 3, 2022, 15 pages.

* cited by examiner

*Primary Examiner* — Si Ming Ku
(74) *Attorney, Agent, or Firm* — Barnes & Thornburg LLP

(57) ABSTRACT

A method, apparatus, and system for balancing a patient's knee joint during an orthopaedic surgical procedure includes measuring a conductance of a medial collateral ligament and a lateral collateral ligament of the patient's knee joint and balancing the tension of the medial and lateral collateral ligaments based on the measured conductance. The tension of the medial and lateral collateral ligaments may be balanced by reducing a difference between the measured conductance.

18 Claims, 11 Drawing Sheets

METHOD, APPARATUS, AND SYSTEM FOR BALANCING A PATIENT'S KNEE JOINT DURING AN ORTHOPAEDIC SURGICAL PROCEDURE

TECHNICAL FIELD

The present disclosure relates generally to orthopaedic surgical procedures, techniques, and associated instruments and, more particularly, to methods, apparatuses, and systems for balancing a patient's knee joint during an orthopaedic surgical procedure.

BACKGROUND

Orthopaedic prostheses are implanted in patients by orthopaedic surgeons to, for example, correct or otherwise alleviate bone and/or soft tissue loss, trauma damage, and/or deformation of the bone(s) of the patients. Orthopaedic prostheses may replace a portion or the complete joint of a patient. For example, the orthopaedic prosthesis may replace the patient's knee, hip, shoulder, ankle, or other joint. In the case of a knee replacement, the orthopaedic knee prosthesis may include a tibial tray, a femoral component, and a polymer insert or bearing positioned between the tibial tray and the femoral component. In some cases, the knee prosthesis may also include a prosthetic patella component, which is secured to a posterior side of the patient's surgically-prepared patella.

During the orthopaedic surgical procedure, a surgeon initially prepares the patient's bone(s) to receive the orthopaedic prosthesis. For example, in the case of a knee replacement orthopaedic surgical procedure, the surgeon may resect a portion of the patient's proximal tibia to which the tibial tray will be attached, a portion of patient's distal femur to which the femoral component will be attached, and/or a portion of the patient's patella to which the patella component will be attached. During such procedures, the surgeon may attempt to balance or otherwise distribute the joint forces of the patient's joint in order to produce joint motion that is similar to the motion of a natural joint or otherwise tracks a desired motion. To do so, the surgeon may use surgical experience and manually "feel" for the appropriate joint force balance. Additionally or alternatively, the orthopaedic surgeon may use surgical instruments, such as a ligament balancer in the case of a knee replacement procedure, to assist in the balancing or distributing of joint forces. Depending the particular procedure, the orthopaedic surgeon may balance the joint forces via various techniques, such as bone shaping or ligament release in the case of a knee replacement procedure.

SUMMARY

According to an aspect of the disclosure, a ligament tension analysis device for monitoring ligament tension of a patient's knee joint includes a first set of probes, a first conductance sensor coupled to the first set of probes, a display, and an analysis circuit. Each probe of the first set of probes is configured to be coupled with a first ligament of the patient's knee joint. The first conductance sensor is configured to produce first conductance data indicative of a conductance of the first ligament of the patient, and the analysis circuit is configured to determine first tension data of the first ligament of the patient based on the first conductance data and display the first tension data on the display. The first tension data may be indicative of an amount of tension of the first ligament of the patient.

In some embodiments, to determine the first tension data of the first ligament of the patient's knee joint may include to determine a first set of tension data values across a range of degrees of flexion of the patient's knee joint. Additionally, each tension value of the first set of tension data values may be indicative of an amount of tension of the first ligament at a corresponding degree of flexion of the patient's knee joint. Further, in some embodiments, to display the first tension data on the display may include to display a tension-versus-flexion graph having a graph curve indicative of the first set of tension data values across the range of degrees of flexion of the patient's knee joint.

Additionally in some embodiments, the ligament tension analysis device may also include a second set of probes and a second conductance sensor. Each probe of the second set of probes may be configured to be coupled with a second ligament of the patient's knee joint. The second conductance sensor is coupled to the second set of probes and may be configured to produce second conductance data indicative of a conductance of the second ligament of the patient. In such embodiments, the analysis circuit may be further configured to determine second tension data for the second ligament of the patient based on the second conductance data and display the second tension data on the display along with the first tension data. The second tension data may be indicative of an amount of tension of the second ligament of the patient.

In some embodiments, to determine the first tension data of the first ligament of the patient may include to determine a first set of tension data values across a range of degrees of flexion of the patient's knee joint. In such embodiments, each tension value of the first set of tension data values may be indicative of an amount of tension of the first ligament at a corresponding degree of flexion of the patient's knee joint. Additionally, to determine the second tension data of the second ligament of the patient's knee joint may include determine a second set of tension data values across the range of degrees of flexion of the patient's knee joint. And, each tension value of the second set of tension data values may be indicative of an amount of tension of the second ligament at a corresponding degree of flexion of the patient's knee joint. Additionally, in such embodiments, to display the first tension data and the second tension data on the display may include to display a tension-versus-flexion graph having a first graph curve indicative of the first set of tension data values across the range of degrees of flexion of the patient's knee joint and a second graph curve indicative of the second set of tension data values across the range of degrees of flexion of the patient's knee joint.

According to another aspect of the disclosure, a ligament coupler for use in measuring an amount of tension of a collateral ligament of a patient's knee joint may include a first right cylindrical half having a first threaded aperture and a second threaded aperture, a second right cylindrical half configured to mate with the first right cylindrical half to form a hollow cylinder having an inner passageway sized to receive the collateral ligament of the patient's knee joint, a first fastener configured to be threaded through the first threaded aperture and into contact with the collateral ligament when the collateral ligament is received in the inner passageway of the hollow cylinder, and a second fastener configured to be threaded through the second threaded aperture and into contact with the collateral ligament when the collateral ligament is received in the inner passageway of the hollow cylinder. In such embodiments, each of the first fastener and the second fastener may include a receptacle configured to mate with a corresponding probe of a ligament tension analysis device.

In some embodiments, each of the first right cylindrical half and the second right cylindrical half may be made from a plastic material, and each of the first fastener and the second fastener is made from a metallic material.

According to a further aspect of the disclosure, a method for performing an orthopaedic surgical procedure on a knee joint of a patient may include measuring a conductance of a medial collateral ligament and a conductance of a lateral collateral ligament of the patient's knee joint. The measured conductance of each collateral ligament may be indicative of an amount of tension of the corresponding medial collateral ligament and lateral collateral ligament. The method may also include balancing the tension of the medial collateral ligament and the tension of the lateral collateral ligament of the patient's knee joint based on the measured conductance of the medial collateral ligament and the measured conductance of the lateral collateral ligament.

Additionally, in some embodiments, balancing the tension of the medial collateral ligament and the tension of the lateral collateral ligament of the patient's knee joint may include performing an orthopaedic surgical procedure on the patient's knee joint to reduce a difference between the measured conductance of the medial collateral ligament and the conductance of the lateral collateral ligament.

In some embodiments, measuring the conductance of the medial collateral ligament and the conductance of the lateral collateral ligament of the patient's knee joint may include operating a ligament tension analysis device to measure the conductance of the medial collateral ligament and the conductance of the lateral collateral ligament of the patient's knee joint, determine first tension data for the medial collateral ligament based on the measured conductance of the medial collateral ligament, wherein the first tension data is indicative of an amount of tension of the medial collateral ligament, determine a second tension data for the lateral collateral ligament based on the measured conductance of the lateral collateral ligament, wherein the second tension data is indicative of an amount of tension of the lateral collateral ligament, and display the first and second tension data on a display. In such embodiments, balancing the tension of the medial collateral ligament and the tension of the lateral collateral ligament of the patient's knee joint may include balancing the tension of the medial collateral ligament and the tension of the lateral collateral ligament to reduce a difference between the first tension data and the second tension data.

Additionally, in some embodiments, balancing the tension of the medial collateral ligament and the tension of the lateral collateral ligament of the patient's knee joint may include balancing the tension of the medial collateral ligament and the tension of the lateral collateral ligament to reduce a difference between first tension data indicative of an amount of tension of the medial collateral ligament and second tension data indicative of an amount of tension of the lateral collateral ligament. The first tension data may be determined based on the measured conductance of the medial collateral ligament and the second tension data is determined based on the measured conductance of the lateral collateral ligament.

In some embodiments, measuring the conductance of the medial collateral ligament and the conductance of a lateral collateral ligament of the patient's knee joint may include measuring the conductance of the medial collateral ligament and the conductance of a lateral collateral ligament across a range of degrees of flexion of the patient's knee joint. In such embodiments, measuring the conductance of the medial collateral ligament and the conductance of the lateral collateral ligament of the patient's knee joint may include operating a ligament tension analysis device to measure the conductance of the medial collateral ligament across the range of degrees of flexion of the patient's knee joint and the conductance of the lateral collateral ligament across the range of degrees of flexion of the patient's knee joint, determine a first set of tension data values for the medial collateral ligament across the range of degrees of flexion of the patient's knee joint based on the measured conductance of the medial collateral ligament, wherein each tension value of the first set of tension data values is indicative of an amount of tension of the medial collateral ligament at a corresponding degree of flexion of the patient's knee joint, determine a second set of tension data values for the lateral collateral ligament across the range of degrees of flexion of the patient's knee joint based on the measured conductance of the lateral collateral ligament, wherein each tension value of the second set of tension data values is indicative of an amount of tension of the lateral collateral ligament at a corresponding degree of flexion of the patient's knee joint, and display a tension-versus-flexion graph having a first graph curve indicative of the first set of tension data values across the range of degrees of flexion of the patient's knee joint and a second graph curve indicative of the second set of tension data values across the range of degrees of flexion of the patient's knee joint. Additionally, in such embodiments, balancing the tension of the medial collateral ligament and the tension of the lateral collateral ligament of the patient's knee joint may include balancing the tension of the medial collateral ligament and the tension of the lateral collateral ligament to reduce an error between the first graph curve and the second graph curve.

In some embodiments, balancing the tension of the medial collateral ligament and the tension of the lateral collateral ligament of the patient's knee joint may include balancing the tension of the medial collateral ligament and the tension of the lateral collateral ligament to reduce an error between a first tension-versus-flexion graph curve indicative of a first set of tension data values of the medial collateral ligament across a range of degrees of flexion of the patient's knee joint and a second tension-versus-flexion graph curve indicative of a second set of tension data values of the lateral collateral ligament across the range of degrees of flexion of the patient's knee joint.

Additionally, in some embodiments, the method may further include coupling a first ligament coupler to the medial collateral ligament and coupling a second ligament coupler to the lateral collateral ligament of the patient's knee joint. In such embodiments, coupling the first ligament coupler to the medial collateral ligament may include encircling the medial collateral ligament with the first ligament coupler. Additionally, in such embodiments, coupling the second ligament coupler to the lateral collateral ligament may include encircling the lateral collateral ligament with the second ligament coupler.

In some embodiments, balancing the tension of the medial collateral ligament and the tension of the lateral collateral ligament may include performing a ligament balancing procedure of the patient's knee joint. Additionally, in such embodiments, performing a ligament balancing procedure of the patient's knee joint comprises may include a ligament release procedure.

Additionally, in some embodiments, balancing the tension of the medial collateral ligament and the tension of the lateral collateral ligament may include periodically monitoring the measured conductance of the medial collateral ligament and the measured conductance of a lateral collateral ligament of the patient's knee joint while performing an orthopaedic surgical procedure on the patient's knee joint.

BRIEF DESCRIPTION OF THE DRAWINGS

The detailed description particularly refers to the following figures, in which.

DETAILED DESCRIPTION OF THE DRAWINGS

Figure 1:
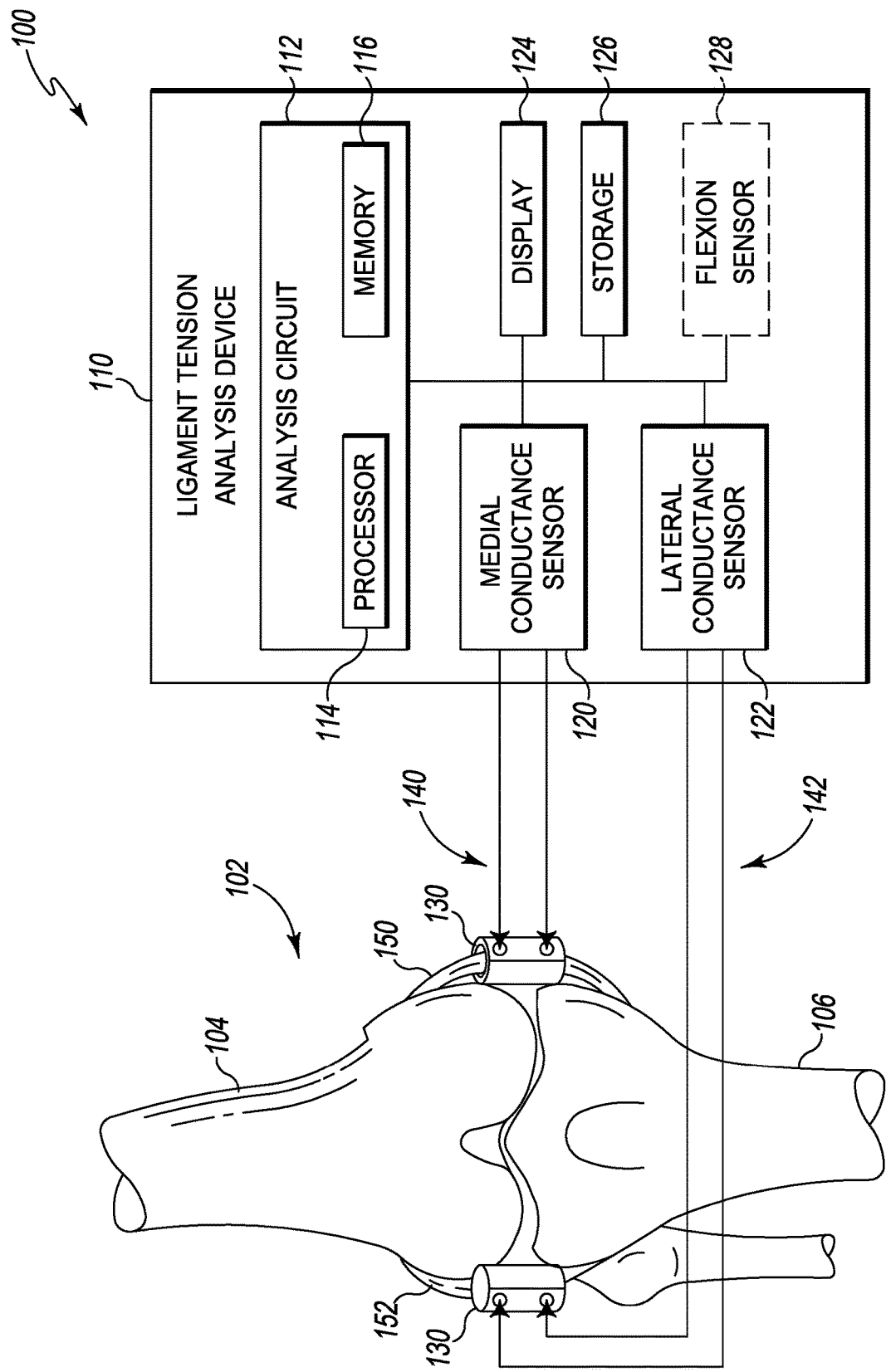
FIG. 1 is a diagram of an embodiment of a system for monitoring ligament tension of a patient's joint during performance of an orthopaedic surgical procedure on the patient's joint.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

Terms representing anatomical references, such as anterior, posterior, medial, lateral, superior, inferior, etcetera, may be used throughout the specification in reference to the orthopaedic implants and surgical instruments described herein as well as in reference to the patient's natural anatomy. Such terms have well-understood meanings in both the study of anatomy and the field of orthopedics. Use of such anatomical reference terms in the written description and claims is intended to be consistent with their well-understood meanings unless noted otherwise. While the disclosure below describes techniques, devices, and systems in reference to a patient's knee joint, it should be appreciated that all of the techniques, devices, and systems described below may be used during an orthopaedic surgical procedure performed on other joints of a patient to balance the respective joint.

References in the specification to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described. Additionally, it should be appreciated that items included in a list in the form of "at least one A, B, and C" can mean (A); (B); (C); (A and B); (A and C); (B and C); or (A, B, and C). Similarly, items listed in the form of "at least one of A, B, or C" can mean (A); (B); (C); (A and B); (A and C); (B and C); or (A, B, and C).

The disclosed embodiments may be implemented, in some cases, in hardware, firmware, software, or any combination thereof. Some disclosed embodiments may also be implemented as instructions carried by or stored on a transitory or non-transitory machine-readable (e.g., computer-readable) storage medium, which may be read and executed by one or more processors. A machine-readable storage medium may be embodied as any storage device, mechanism, or other physical structure for storing or transmitting information in a form readable by a machine (e.g., a volatile or non-volatile memory, a media disc, or other media device).

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

Referring now to FIG. 1, in an illustrative embodiment, a system 100 for monitoring ligament tension (i.e., strain) of a patient's knee joint 102 includes a ligament tension analysis device 110 and a pair of ligament couplers 130. As discussed in more detail below, the ligament tension analysis device 110 is configured to determine a relative tension of the collateral ligaments of the patient's knee joint 102 based on a measured electrical conductance of each corresponding ligament. It should be appreciated that the electrical conductance of dense fibrous tissue, such as ligaments, changes as strain on the tissue changes due to various factors including tissue hydration and strain-impeded electrical and solute transport. As such, the electrical conductance of a ligament is indicative of the amount of strain or tension presentably experienced by the corresponding tissue.

Accordingly, as discussed in more detail below, an orthopaedic surgeon may utilize the ligament tension analysis device 110 during performance of an orthopaedic surgical procedure (e.g., a total or unicompartmental knee arthroplasty procedure) to improve the balancing of the patient's knee joint 102 by monitoring and correspondingly adjusting the tension (i.e., strain) of the relevant collateral ligaments. To do so, the orthopaedic surgeon may operate the ligament tension analysis device 110 to measure the present electrical conductance of the ligaments of the patient's knee joint 102 pre-operatively and/or intra-operatively to facilitate proper balancing of the patient's knee joint 102. For example, the orthopaedic surgeon may couple a ligament coupler 130 to each of the medial collateral ligament (MCL) 150 and the lateral collateral ligament (LCL) 152 of the relevant knee joint 102 of the patient and connect each ligament coupler 130 to the ligament tension analysis device 110. As discussed in more detail below, the ligament couplers 130 facilitate connection of the ligament tension analysis device 110 with the tissue of the medial and lateral collateral ligaments 150, 152.

After the ligament tension analysis device 110 has been connected to the collateral ligaments 150, 152 of the patient's knee joint 102 via the ligament couplers 130, the orthopaedic surgeon may operate the ligament tension analysis device 110 to determine and display tension data indicative of the tension of each of the medial and lateral collateral ligaments 150, 152 of the patient's knee joint 102. To do so, the ligament tension analysis device 110 measures the electrical conductance of each collateral ligament 150, 152, determines tension data that is indicative of the present tension of the corresponding collateral ligament 150, 152 based on the measured conductance, and displays the determined tension data on a display for viewing by the orthopaedic surgeon. As such, the orthopaedic surgeon may monitor the display of the tension data during the performance of the orthopaedic surgery to ensure the tension of the collateral ligaments 150, 152 is properly balanced. For example, the orthopaedic surgeon may perform various surgical techniques (e.g., bone resection) to reduce a difference between the displayed tension data of the medial and lateral collateral ligaments 150, 152. It should be appreciated that because conductance measurement values are indicative of the present tension (i.e., strain) of the medial and lateral collateral ligaments 150, 152 as discussed above, reducing the difference between the respective conductance measurement values (i.e., between tension data that is indicative of such values) improves the balance of tension between the medial and lateral collateral ligaments 150, 152.

In some embodiments, the ligament tension analysis device 110 is configured to determine tension data (e.g., conductance values) for each of the medial and lateral collateral ligaments 150, 152 of the patient's knee joint 102 across a range of degrees of flexion (rather than, or in addition to, a single point in time) and displays a tension-versus-flexion graph for viewing by the orthopaedic surgeon. To do so, the orthopaedic surgeon may pivot the patient's knee joint 102 through the range of degrees of flexion while the ligament tension analysis device 110 measures the electrical conductance of the medial and lateral collateral ligaments 150, 152 at corresponding degrees of flexion. In such embodiments, the orthopedic surgeon may balance the patient's knee joint by performing the various surgical techniques to reduce an error between graph curves of the tension-versus-flexion graph that are indicative of the conductance values of the medial and lateral collateral ligaments 150, 152 of the patient's knee joint 102 across the range of degrees of flexion.

The ligament tension analysis device 110 may be embodied as any type of device or collection of devices capable of measuring and analyzing the electrical conductance of a patient's ligament and performing the other functions described herein. In some embodiments, the ligament tension analysis device 110 may be embodied as a computing device, such as a laptop computer, a mobile computer, a desktop computer, a workstation, a server, a special-built computer, a tablet computer, or other computer or computing device. In other embodiments, the ligament tension analysis device 110 may be embodied as a special-built computer or computing device and, in some embodiments, may form a portion of another computer or computing device or an orthopedic surgical instruction such as a distractor as discussed in more detail below. For example, the ligament tension analysis device 110, or portion thereof, may be embodied as an embedded system, an integrated circuit, a field-programmable-array (FPGA), a system-on-a-chip (SOC), or other integrated system or device, which may be a stand-alone device or be included in a more general computing device.

In the illustrative embodiment, the ligament tension analysis device 110 includes an analysis circuit 112, a medial conductance sensor 120, a lateral conductance sensor 122, a display 124, a storage device 126, and, in some embodiments, a flexion sensor 128. Of course, in other embodiments, the ligament tension analysis device 110 may include other or additional components, such as those commonly found in a computer (e.g., input device(s), output device(s), peripheral devices, etc.). Additionally, in some embodiments, one or more of the illustrative components may be incorporated in, or otherwise form a portion of, another component.

The analysis circuit 112 may be embodied as any type of circuit, device, or collection of devices capable of performing various analytical and/or computing functions described herein. In some embodiments, the analysis circuit 112 may be embodied as a single device such as a microcontroller, an integrated circuit, an embedded system, a field programmable gate array (FPGA), a system-on-a-chip (SOC), or other integrated system or device. Additionally, in some embodiments, the analysis circuit 112 includes or is embodied as a processor 114 and a memory 116. The processor 114 may be embodied as one or more processors, each processor being a type capable of performing the functions described herein. For example, the processor 114 may be embodied as a single or multi-core processor(s), a microcontroller, or other processor or processing/controlling circuit. In some embodiments, the processor 114 may be embodied as, include, or be coupled to an FPGA, an ASIC, reconfigurable hardware or hardware circuitry, or other specialized hardware to facilitate performance of the functions described herein. The memory 116 may be embodied as any type of volatile (e.g., dynamic random access memory, etc.) or non-volatile memory (e.g., byte addressable memory) or data storage capable of performing the functions described herein.

Each of the medial conductance sensor 120 and the lateral conductance sensor 122 may be embodied as any type of sensor or sensing circuitry capable of measuring a conductance of a corresponding ligament of the patient's knee joint 102 and producing data indicative of the measured conductance. To do so, the conductance sensors 120, 122 may utilize any suitable methodology to measure the electrical conductance of the medial and lateral collateral ligaments of the patient's knee joint 102. For example, in the illustrative example, the ligament tension analysis device 110 is configured to generate a five (5V) voltage across outputs of each sensor 120, 122 and measure the resulting current. The measured current may then be used to determine a measured resistance according to Ohm's law and the resulting conductance can be determined as the reciprocal of the measured resistance (or determined directly from the measured current). Of course, in other embodiments, analysis signals of different voltages and/or current may be used to measure the conductance of the ligaments to the collateral ligaments 150, 152.

Each of the conductance sensors 120, 122 is connected to a corresponding set of electrical leads 140, 142, each of which are connected to a corresponding electrical coupler 130 as discussed in more detail below. Although the conductance sensors 120, 122 are shown as being included in the ligament tension analysis device 110 in FIG. 1, the conductance sensors 120, 122 may be external to the ligament tension analysis device 110 in other embodiments. For example, each conductance sensor 120, 122 may be located at a distal end of the corresponding electrical lead 140, 142 in some embodiments. Additionally, although the ligament tension analysis device 110 is shown as including a conductance sensor 120, 122 for each of the medial and lateral collateral ligaments 150, 152, it should be appreciated that the ligament tension analysis device 110 may include a single conductance sensor 120 and a single set of electrical leads 140 (i.e., the analysis device 110 may not include the conductance sensor 122 and the electrical leads 142) connected to the single conductance sensor 140. In such embodiments, the single set of electrical leads 140 may be used to measure the conductance of each of the medial and lateral collateral ligaments 150, 152 in a sequential fashion. That is, the conductance of one of the medial or lateral collateral ligament 150, 152 may be measured using the single set of electrical leads 140, followed by the other one of the medial or lateral collateral ligament 150, 152.

The display 124 of the ligament tension analysis device 110 may be embodied as any type of display capable of displaying digital information such as a liquid crystal display (LCD), a light emitting diode (LED), a plasma display, a cathode ray tube (CRT), or other type of display device. In some embodiments, the display 124 may include a touch screen to allow user interaction with the ligament tension analysis device 110. As discussed in more detail below, during operation of the ligament tension analysis device 110, the display 124 may display conductance values indicative of the present amount of tension in the medial and lateral collateral ligaments 150, 152 of the patient's knee joint 102 and/or a conductance-verse-flexion graph(s) indicative of conductance values of the medial and lateral collateral ligaments 150, 152 across a range of degrees of flexion. Although shown as included in the ligament tension analysis device 110 in FIG. 1, it should be appreciated that the display 124 may be separate from but communicatively coupled to the ligament tension analysis device 110 in other embodiments.

The data storage 126 may be embodied as any type of device or devices configured for short-term or long-term storage of data. For example, the data storage 126 may be embodied as, or otherwise include, memory devices and circuits, memory cards, hard disk drives, solid-state drives, or other data storage devices.

In embodiments in which the ligament tension analysis device 110 is configured to generate the tension-versus-flexion graph, the ligament tension analysis device 110 may also include one or more flexion sensors 128. Each of the flexion sensors 128 may be embodied as any type of sensor capable of producing sensor data indicative of the present degree of flexion of the patient's knee joint 102 (e.g., a measurement of an angle defined between the patient's femur 104 and tibia 106 of the knee joint 102). For example, the flexion sensors 128 may be embodied as optical sensors configured to generate sensor data indicative of the present degree of flexion of the patient's knee joint 102 based on one or more images or image data. In such embodiments, additional devices, such as optical markers, may be used and attached to the boney anatomy of the patient to facilitate the determination of the present degree of flexion of the patient's knee joint 102.

Figure 2:
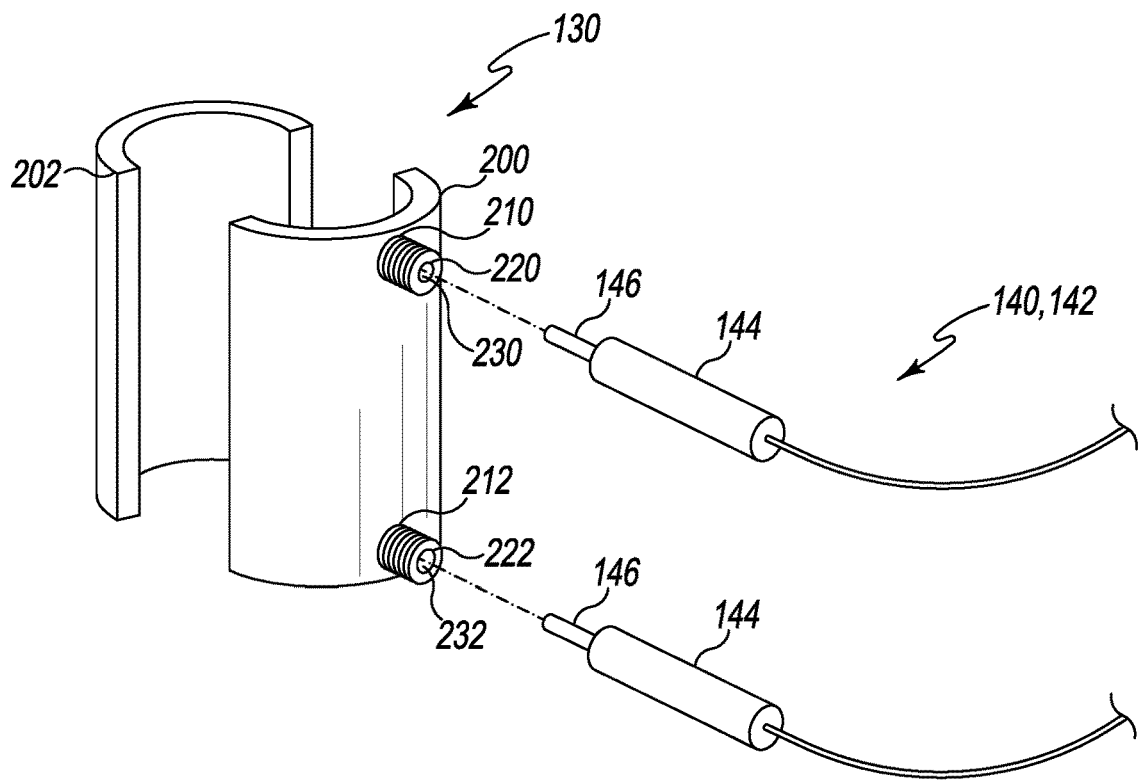
FIG. 2 is a perspective view of an embodiment of a ligament coupler of the system of FIG. 1, which is configured to couple to a ligament of the patient's knee joint.

Referring now to FIG. 2, in the illustrative embodiment, each of the ligament coupler 130 is designed to electrically insulate the corresponding ligament of the patient's knee joint 102 from other surrounding tissue and provide a mechanism by which the sets of leads 140, 142 of the ligament tension analysis device 110 can be electrically connected to the corresponding medial and lateral collateral ligament. Illustratively, each ligament coupler 130 is shaped as a hollow cylinder having a two longitudinal cylindrical halves 200, 202, which when mated together form the hollow cylinder. Each of the longitudinal cylindrical halves 200, 202 is illustratively formed from a plastic material to provide some amount of electrical insulation to the other nearby tissue.

As shown in FIG. 2, one of the longitudinal cylindrical halves 200, 202 (illustratively half 202) includes a pair of threaded apertures 210, 212 located on distal ends of the longitudinal half cylinder. The ligament coupler 130 includes a corresponding pair of fasteners 220, 222, such as screws, configured to be received in the threaded apertures 210, 212. Each of the fasteners 220, 222 includes a corresponding receptacle 230, 232 at an external end, which is configured to mate or couple with one of the sets of leads 140, 142 of the ligament tension analysis device 110. To facilitate such connection, each lead of the sets of leads 140 includes a plug 144 having a terminal 146 configured to mate or otherwise connect with the corresponding receptacles 230, 232 of the fasteners 220, 222.

Figure 3:
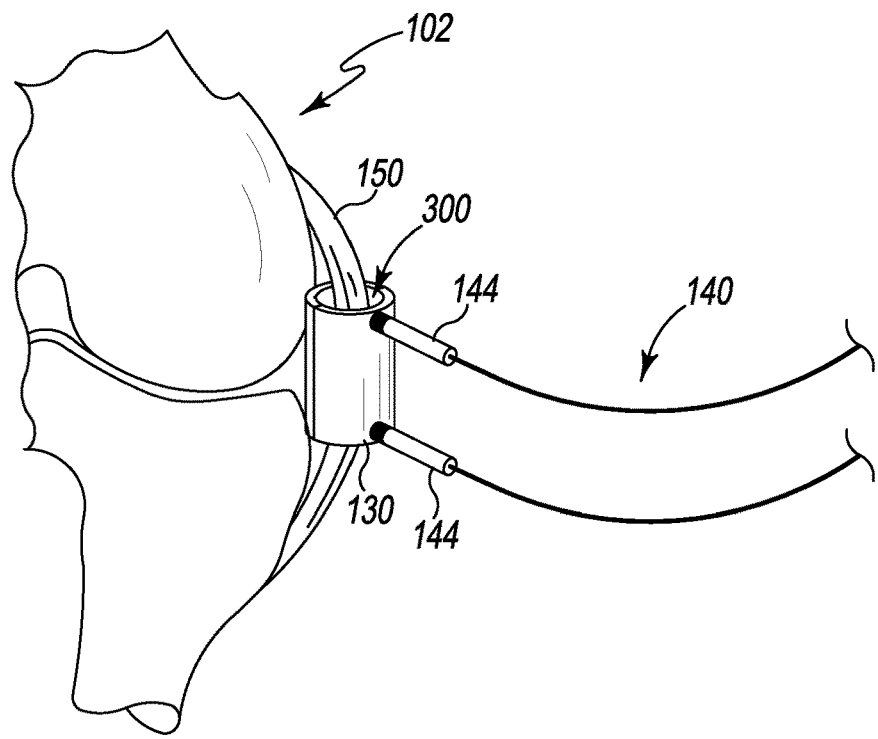
FIG. 3 is an elevation view of the ligament coupler of FIG. 2 coupled to a collateral ligament of the patient's knee joint.

In use, the orthopaedic surgeon may couple a ligament coupler 130 to each of the medial and lateral collateral ligaments 150, 152 of the patient's knee joint 102. To do so, as shown in FIG. 3 with respect to the medial collateral ligament 150, the orthopaedic surgeon may position each of the two longitudinal cylindrical halves 200, 202 of the ligament coupler 130 around the medial collateral ligament 150 such that cylindrical halves 200, 202 encircle the medial collateral ligament 150. The two cylindrical halves 200, 202 are then coupled together (e.g., even corresponding screws, lock, or other mechanism) to form the hollow cylinder having an internal passageway 300 through which the medial collateral ligament 150 extends. The orthopaedic surgeon then threads the fasteners 220, 222 into the threaded apertures 210, 212 of the corresponding ligament coupler 130 such that a distal end of each fastener 220, 222 contacts or embeds into the medial collateral ligament 150 to thereby ensure proper electrical contact to the tissue. The orthopaedic surgeon may then couple the corresponding set of leads 140, 142 by connecting the terminal 146 of each plug 144 of the corresponding set of leads 140, 142 to a corresponding one of the receptacles 220, 232 of the fasteners 220, 222.

Figure 4:
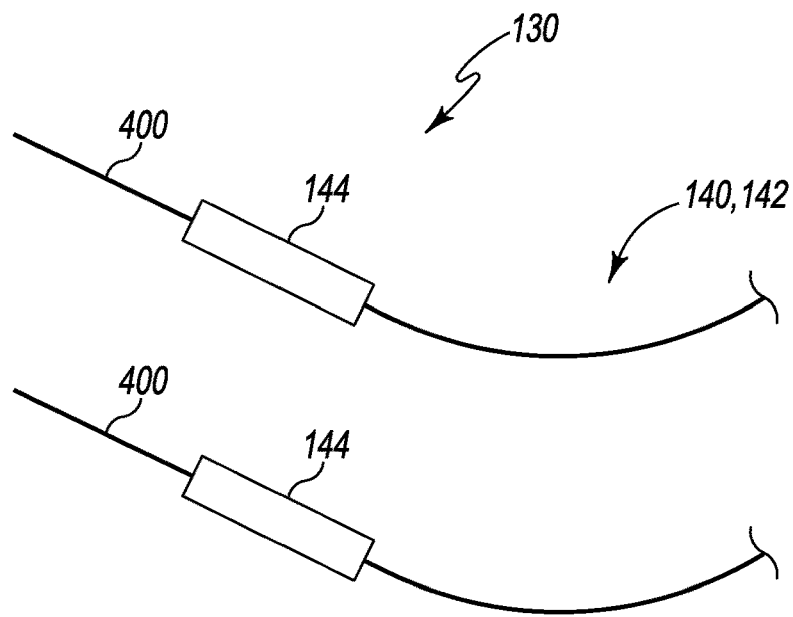
FIG. 4 is a perspective view of another embodiment of a ligament coupler of the system of FIG. 1 configured to couple to a ligament of the patient's knee joint.
Figure 5:
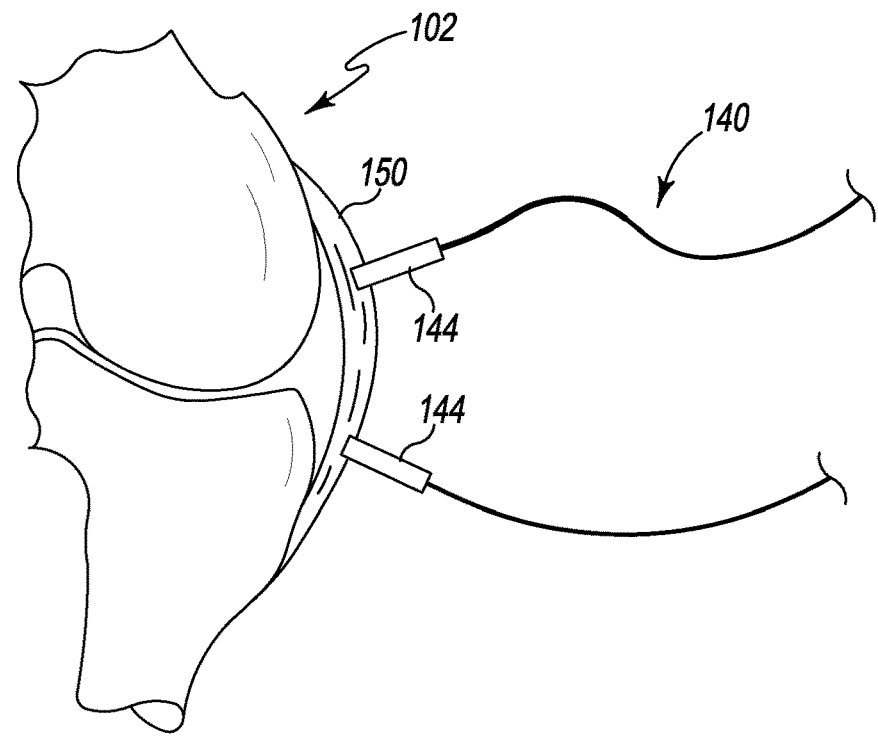
FIG. 5 is an elevation view of the ligament coupler of FIG. 4 coupled to a collateral ligament of a patient's knee joint.

Referring now to FIGS. 4 and 5, in another embodiment, each of the ligament couplers 130 may be embodied as simple plugs 144 connected to the distal ends of the sets of leads 140, 142. Each of the plugs 144 includes a connection needle 400, which is configured to be inserted into the corresponding ligament of the patient's knee joint 102 to establish electrical contact with the tissue. For example, as shown in FIG. 5, a connection needle 400 is injected into a superior end of the medial collateral ligament 150 of the patient's knee joint 102 and another connection needle 400 is injected into an inferior end of the medial collateral ligament 150.

In either embodiment of FIGS. 2 and 3 or FIGS. 4 and 5, the connection location of plugs 144 into the collateral ligaments 150, 152 is generally selected such that the analysis signal can be properly transmitted between the plugs 144. For example, the connection location of the plugs 144 may be selected such that the plugs of a corresponding set of leads 140, 142 are close to each other and toward the inferior-superior center of the corresponding collateral ligament 150, 152. Regardless, it should be appreciated that the connection location of the plugs 144 should be the same or similar between any pre-operative, intra-operative, and post-operative measurements to ensure accuracy of relative measurements.

Figure 6:
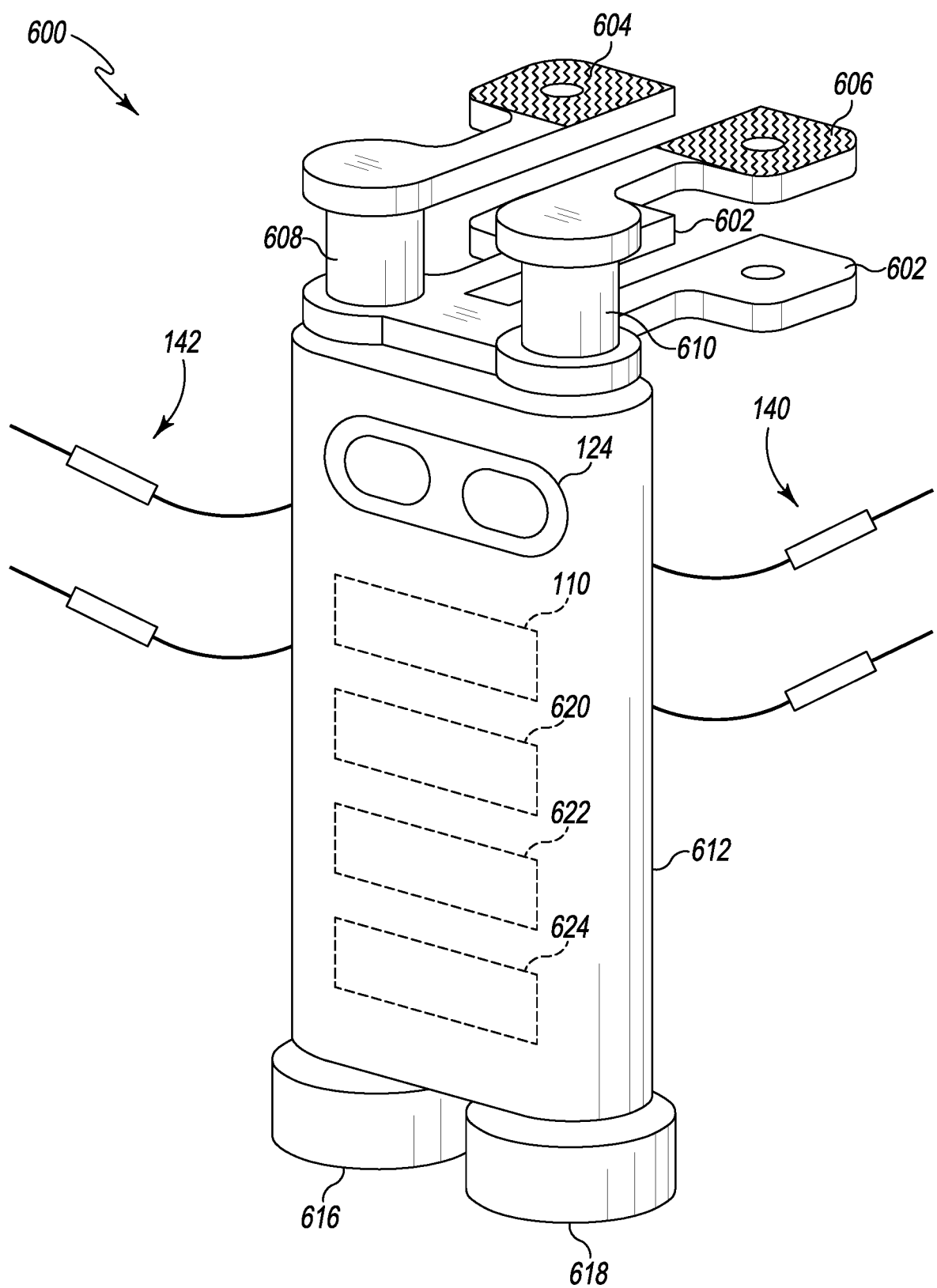
FIG. 6 is a perspective view of an embodiment of a ligament balancer having a ligament tension analysis device of the system of FIG. 1 incorporated therein.

In some embodiments, the ligament tension analysis device 110 (or portions thereof), may be included in other devices, such as other orthopaedic surgical instruments. For example, in some embodiments as shown in FIG. 6, the ligament tension analysis device 100 may be included in a ligament balancer 600, which may be manually and/or automatically operable to distract the patient's knee joint 102 and provide measurement of ligament tension using the ligament tension analysis device 110. The ligament balancer 600 includes a tibial paddle 602, a first femoral paddle 604, and a second femoral paddle 606. The tibial paddle 602 is configured to contact a proximal tibia of the patient, and the femoral paddles 604, 606 are configured to contact a distal femur of the patient. Each of the femoral paddles 604, 606 is positioned vertically over and independently movable away from the tibial paddle 602.

In use, one of the femoral paddles 604, 606 contacts the medial side of the patient's femur 104 and the other femoral paddle 604, 606 contacts the lateral side of the patient's femur 104 depending on which knee joint of the patient is being operated on. For the following description, it will be assumed that the ligament balancer 600 is being used on a patient's left knee. Accordingly, femoral paddle 604 and components associated therewith may be described hereinafter as medial femoral paddle 604 and components. Similarly, the femoral paddle 606 and components associated therewith may be described hereinafter as lateral femoral paddle 606 and components.

Each of the femoral paddles 604, 606 is coupled to respective cylinders 608, 610. The cylinders 608, 610 are extendable out of and retractable into a housing 612. As such, the medial femoral paddle 604 may be moved away from or toward the tibia paddle 602 by extending or retracting the cylinder 608. Similarly, the lateral femoral paddle 606 may be moved away from or toward the tibia paddle 602 by extending or retracting the cylinder 610. It should be appreciated that each femoral paddle 604, 606 is independently movable.

Movement of the femoral paddles 604, 606 may be performed via manual or automated means. For example, in some embodiments, the ligament balancer 602 includes knobs 616, 618 operatively coupled, such as by a screw mechanism, to the cylinders 608, 610, respectively. By manually turning one or both knobs 616, 618 in a clockwise or counterclockwise direction, the cylinders 608, 610 may be extended from or retracted into the housing 612 so as to move the femoral paddles 604, 606. In other embodiments, additional or alternative devices for manually moving the femoral paddles 604, 606 toward and away from the tibial paddle 602 may be included. As will be described below in greater detail, in yet other embodiments, such manual adjustment of the ligament balancer 600 may be replaced or included with automated mechanisms.

As discussed above, the illustrative ligament balancer 600 includes the ligament tension analysis device 110, which is located within the housing 612. The display 124 of the ligament tension analysis device 110 is located on an external surface of the housing 612 to allow a user to view the tension data displayed on the display during a balancing procedure as discussed in more detail below. Additionally, the electrical leads 140, 142 extend form the housing 612 and are configured to be inserted into the medial and lateral collateral ligaments 150, 152 of the patient as discussed above.

In embodiments in which the ligament balancer 600 is automatically adjustable, the ligament balancer 600 may also include a controller 620, a pair of actuators 622, and a power supply 624. Of course, the ligament balancer 600 may include additional components (e.g., sensors), devices, and circuitry in other embodiments depending on the desired functionality of the ligament balancer 600.

The controller 620 may be embodied as any type of circuitry and/or electronic device capable of controlling the functionality of the ligament balancer 600. For example, the controller 620 may be embodied as a processor, a general purpose micro-controller, a microprocessor, an application specific integrated circuits (ASICs), or other control circuit or device. The controller 620, and other electrical components of the ligament balancer 600, receive power from the power supply 624, which may be embodied as type of suitable power supply device. For example, in one particular embodiment, the power supply 624 is embodied as replaceable batteries. In another embodiment, the power supply 624 is embodied as rechargeable battery packs. In such embodiments, the ligament balancer 600 may include appropriate charging contacts to allow the recharging of the battery packs.

The actuators 622 may be embodied as any suitable type of prime mover devices capable of moving the cylinders 608, 610 and thereby, the femoral paddles 604, 606. That is, each actuator 622 is coupled to a corresponding one of the cylinders 608, 610 and is operable to extend or retract the corresponding cylinder 608, 610 in response to a corresponding control signal from the controller 620. In one particular embodiment, the actuators 622 are embodied as stepper motors. In another embodiment, the actuators 622 are embodied as linear actuators. However, the actuators 622 may be embodied as any prime mover devices operable to extend or retract the cylinders 608, 610.

In use, an orthopaedic surgeon may insert the ligament balancer 600 into a resected knee joint 102 of the patient and operate the ligament balancer 600 to distract the patient's knee. For example, the orthopaedic surgeon may distract the patient's knee with the ligament balancer 600 so as to balance the medial and lateral tension (i.e., strain) of the knee joint 102 as reported by the ligament tension analysis device 110 and discussed in more detail below (e.g., by balancing the displayed tension data of the medial and lateral collateral ligaments 150, 152). In embodiments in which the ligament balancer 600 is manually operated, the orthopaedic surgeon may operate the knobs 616, 618 to move the femoral paddles 604, 606 to distract the patient's knee joint 102. Alternatively, in embodiments in which the ligament balancer is motorized, the orthopaedic surgeon may control the ligament balancer 600 to cause the actuators 622 to independently move the femoral paddles 604, 606 to distract the patient's knee joint. In such embodiments, the ligament balancer 600 may be programmed, or otherwise configured, to automate the distraction procedure by automatically moving the femoral paddles 604, 606 until the tension data of the medial and lateral collateral ligaments 150, 152 is equalized or within a threshold of each other as discussed in more detail below.

Figure 7A:
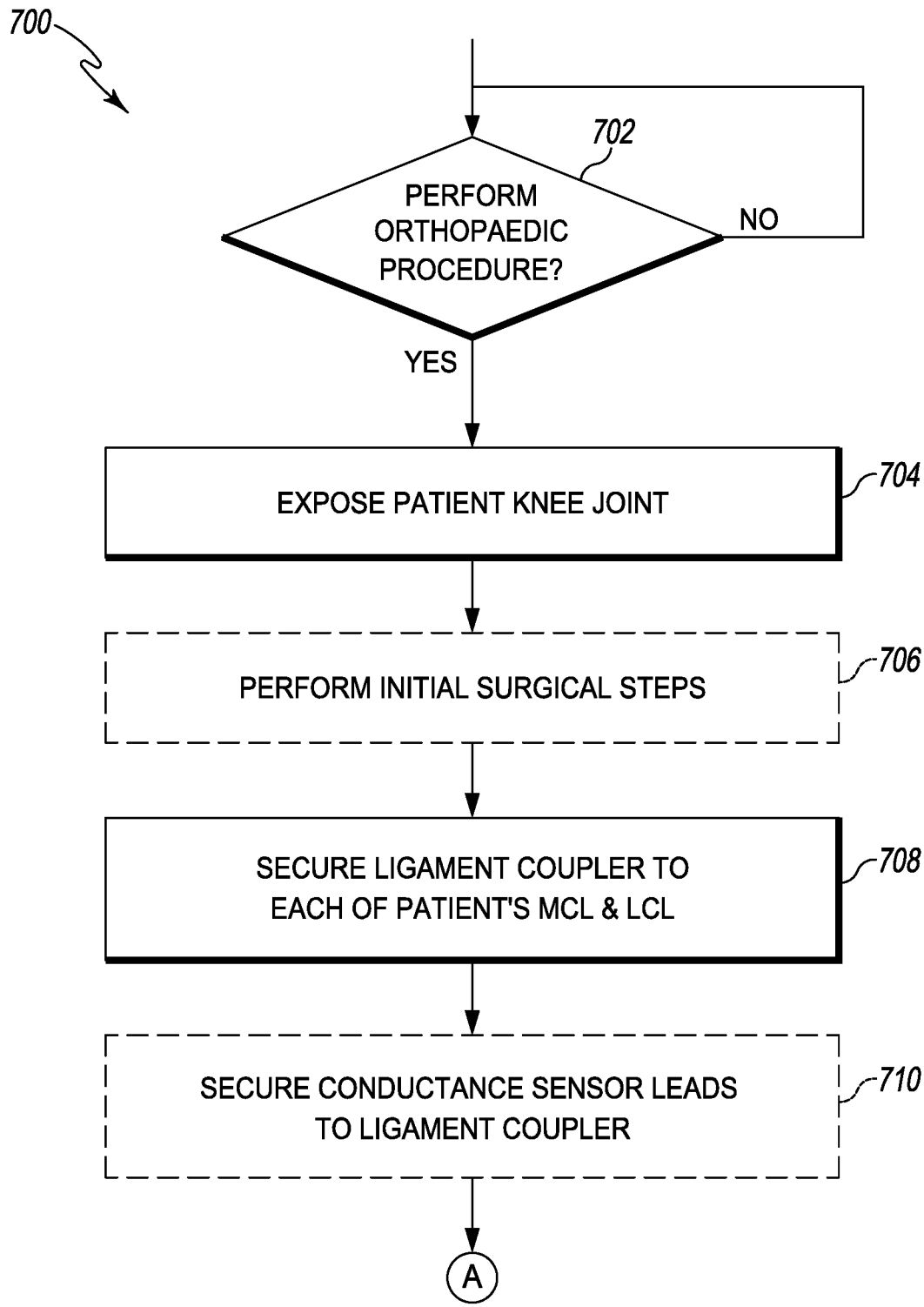
FIGS. 7A-7C are a simplified flow diagram of an embodiment of a method for performing an orthopaedic surgical procedure on a knee joint of a patient using the system of FIG. 1.
Figure 7B:
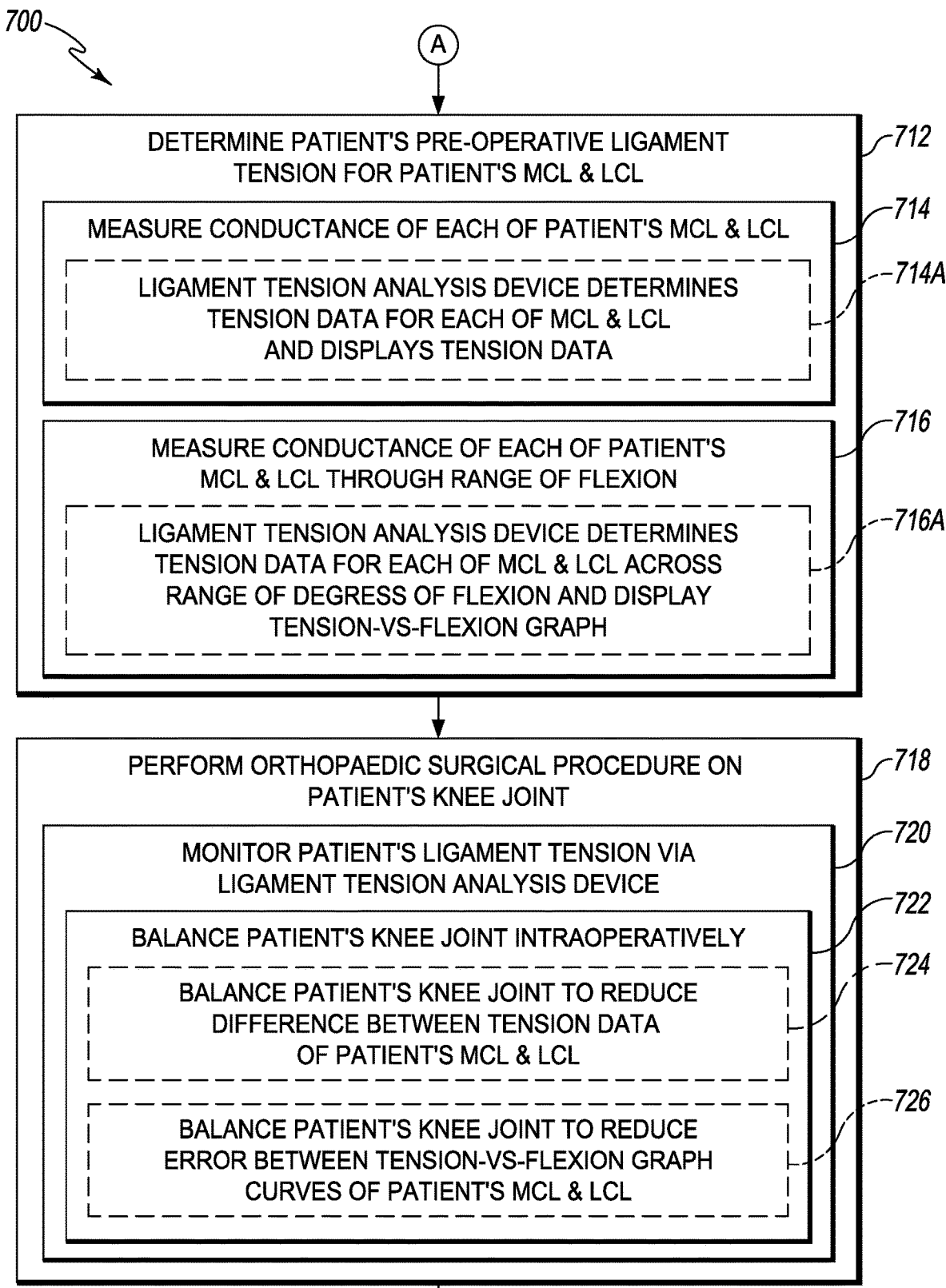
Figure 7C:
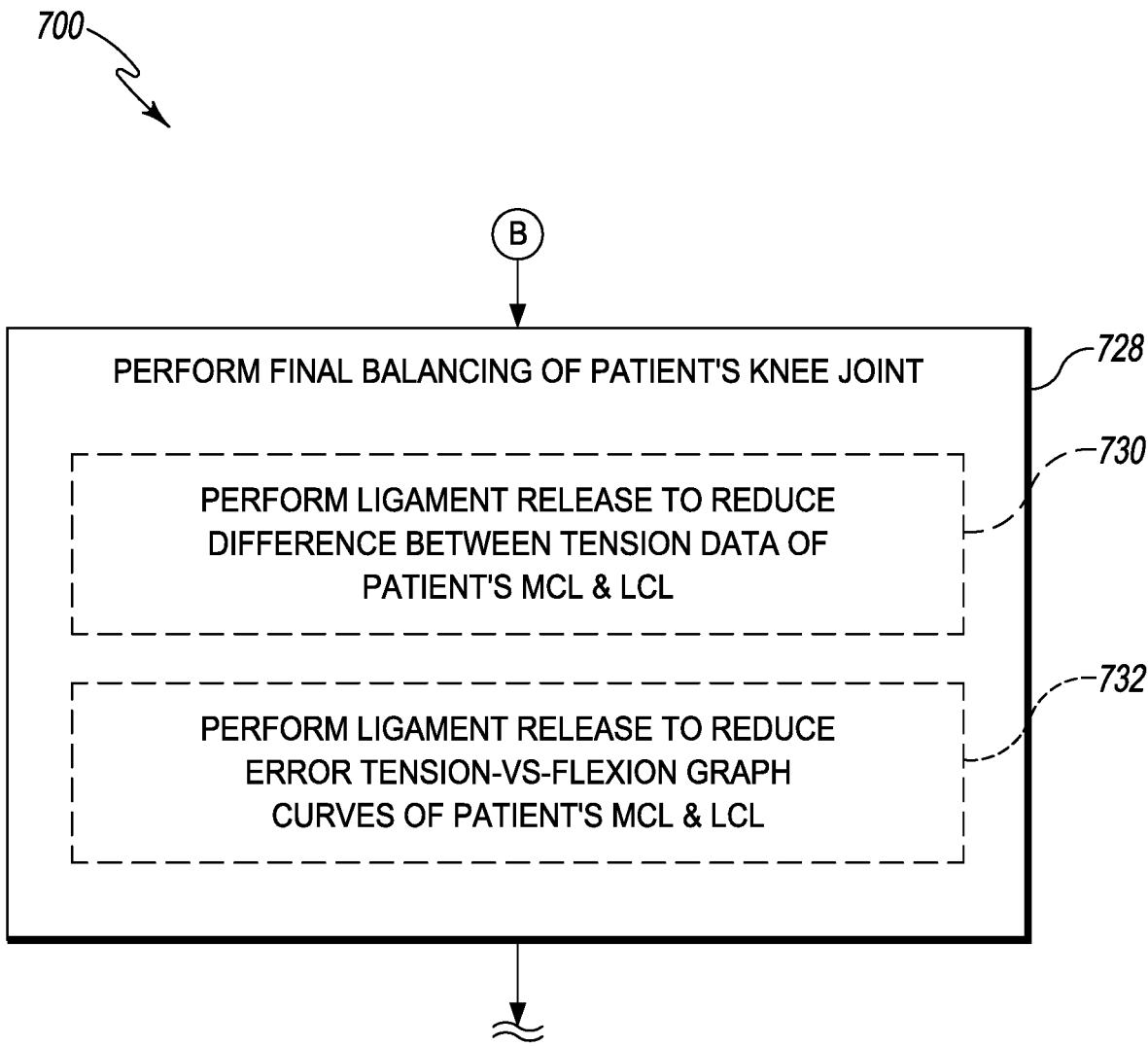

Referring now to FIGS. 7A-7C, a surgical method 700 for performing an orthopaedic surgical procedure on a patient's knee joint 102 using the ligament tension analysis device 110 is shown. The method 700 begins with block 702 in which the orthopaedic surgeon determines whether to begin the orthopaedic surgical procedure. The ligament tension analysis device 110 may be utilized to perform any one of a number of surgical procedures on a joint of the patient. Illustratively, the surgical method 600 includes a total or unicompartmental knee arthroplasty (TKA or UKA) on the patient's knee joint 102 in which the distal end (or portion thereof in the case of a UKA) of the patient's femur 104 and/or the proximal end (or portion thereof in the case of a UKA) of the patients tibia is replaced with a orthopaedic prosthetic. In such surgical procedures, ensuring tension balance (i.e., strain balance) between the medial collateral ligament 150 and lateral collateral ligament 152 of the patient's knee joint 102 can result in a more natural or otherwise improved motion of the patient's knee joint 102 post-operatively.

If the orthopaedic surgeon determines to begin the orthopaedic surgical procedure in block 700, the orthopaedic surgeon exposes the patient's knee joint 102 in block 604. Additionally, in some embodiments, in block 706, the orthopaedic surgeon may perform some initial surgical steps, depending on the particular orthopaedic surgical procedure.

Regardless, in block 708, the orthopaedic surgeon secures a ligament coupler 130 to each of the medial collateral ligament 150 and the lateral collateral ligament on the patient's knee joint 102 on which the surgical procedure is being performed. To do so, in embodiments in which the ligament couplers 130 are embodied as cylindrical couplers as shown in FIGS. 2 and 3, the orthopaedic surgeon may position each of the two longitudinal cylindrical halves 200, 202 of one of the ligament couplers 130 around the medial collateral ligament 150 such that cylindrical halves 200, 202 encircle the medial collateral ligament 150 and each of the two longitudinal cylindrical halves 200, 202 of the other one of the ligament couplers 130 around the lateral collateral ligament 152 such that cylindrical halves 200, 202 encircle the lateral collateral ligament 152 as shown in FIG. 3. The orthopaedic surgeon then threads the fasteners 220, 222 into the threaded apertures 210, 212 of each cylindrical half 200 to establish electrical contact with each of the medial collateral ligament 150 and lateral collateral ligament 152 as discussed above. Subsequently, in block 710, the orthopaedic surgeon connects one set of leads 140, 142 to the receptacles 220, 232 of the fasteners 220, 220 in each of the cylindrical halves 200 as discussed above.

Alternatively, in embodiments in which the ligament couplers 130 are embodied as plugs 144 including the needles 400 as shown above in FIG. 4, the orthopaedic surgeon may connect each plug 144 directly to the corresponding medial collateral ligament 150 or lateral collateral ligament 152. To do so, as shown and discussed above in regard to FIG. 5, the orthopaedic surgeon may inject a connection needle 400 into a superior end of the corresponding medial and lateral collateral ligament 150, 152 and another connection needle 400 into an inferior end of the corresponding medial and lateral collateral ligament 152.

Regardless, after the ligament couplers 130 have been secured to the medial and lateral collateral ligaments 150, 152 of the patient's knee joint 112 in block 708, the orthopaedic surgeon determines the pre-operative tension of each of the medial collateral ligament 150 and the lateral collateral ligament 152 of the patient's knee joint 102 in block 712. To do so, the orthopaedic surgeon may operate the ligament tension analysis device 110 to measure the electrical conductance of each of the medial collateral ligament 150 and the lateral collateral ligament 152 in block 614.

In response, in block 714A and as discussed in more detail below in regard to method 1300 of FIG. 13, the ligament tension analysis device 100 measures the electrical conductance of the patient's medial collateral ligament 150 and the lateral collateral ligament 152, determines tension data for each of the collateral ligaments 150, 152 based on the measured conductance, and displays the tension data. For example, as shown FIG. 8, the ligament tension analysis device 110 may display an interface 800 that includes tension data 802 for the medial collateral ligament 150 and a tension data 804 for the lateral collateral ligament 152. As discussed above, the tension data 802, 804 is indicative of the tension of the corresponding collateral ligaments 150, 152 and are based on the measured conductance of those collateral ligaments 150, 152. In some embodiments, the tension data 802, 804 may be embodied as the raw conductance measurement values (e.g., measured in siemens) or embodied as other numerical values based on the conductance. For example, in some embodiments, the tension data 802, 804 may be embodied as numerical values determined based on a quantization of the measured conductance or based on an output of a mathematical algorithm to which the measured conductance value is an input. Further, in some embodiments, the tension data may be displayed as a graphical representation as discussed below or non-numeric data that is indicative of the tension or relative tension of the collateral ligaments 150, 152. For example, in some embodiments, the particular color (e.g., green) may be displayed in the display 180 for each collateral ligaments 150, 152 if the measured conductance value is within a pre-defined range or within a predefined threshold of each other. Regardless, it should be appreciated that the difference in the displayed tension data 802, 804 is indicative of the relative difference in tension of the medial and lateral collateral ligaments 150, 152.

Referring back to FIG. 7B, in some embodiments, the orthopaedic surgeon may operate the ligament tension analysis device 110 to measure the electrical conductance of each of the medial collateral ligament 150 and the lateral collateral ligament 152 across a range of degrees of flexion in block 716. To do so, the orthopaedic surgeon may pivot or otherwise move the patient's knee joint 102 through the desired range of degrees of flexion while the ligament tension analysis device 110 measures the electrical conductance of each of the medial and lateral collateral ligaments 150, 152 across the range of degrees of flexion using the conductance sensors 120, 122 and the flexion sensor 128, as shown in block 716A.

Figure 9:
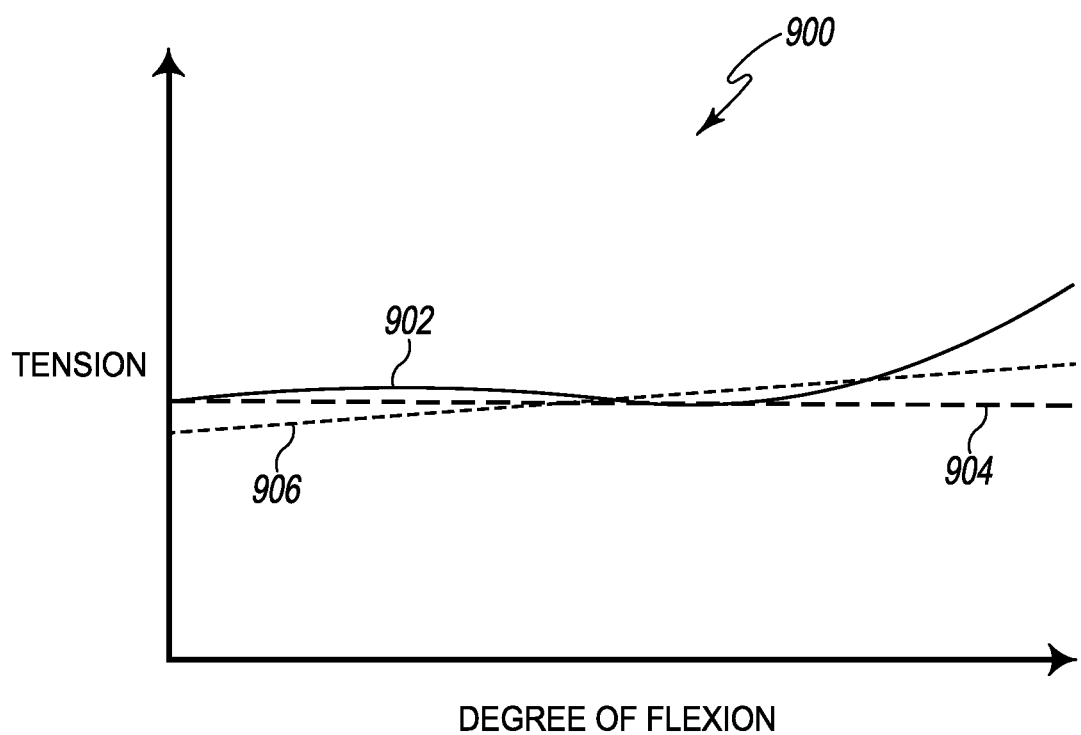
FIG. 9 is a tension-versus-flexion graph illustrating tension of a collateral ligament of the patient's knee joint across a range of degrees of flexion.

Additionally, in block 716A, the ligament tension analysis device 110 may display a tension-versus-flexion graph on the display 124, which the orthopaedic surgeon may use to facilitate the balancing of the patient's knee joint 102. For example, as shown in FIG. 9, the ligament tension analysis device 110 may display a tension-versus-flexion graph 900 for one of the medial or lateral collateral ligaments 150, 152. The illustrative tension-versus-flexion graph 900 includes a graph curve 902 illustrating the tension data (e.g., measured conductance values or values (quantized values) determined based on the measured conductance) for the corresponding medial or lateral collateral ligaments 150, 152, which are indicative of corresponding ligament tension, at the varying degrees of flexion. Additionally, the tension-versus-flexion graph 900 may include one or more target curves that identify desired tension (e.g., conductance values) across the range of degrees of flexion. For example, the tension-versus-flexion graph 900 includes an illustrative target graph curve 904 that identifies a relative linear tension data-to-flexion relationship. Alternatively, the tension-versus-flexion graph 900 also includes a target graph curve 906 that identifies a another desired tension data-to-flexion relationship.

Regardless, as discussed in more detail below, it should be appreciated that the orthopedic surgeon may utilize the tension-versus-flexion graph 900 to balance the tension of the corresponding medial or lateral collateral ligament 150, 152 across the range of degrees of flexion by reducing the error between the graph curve 902 illustrating the tension (e.g., conductance values) for the corresponding medial or lateral collateral ligaments 150, 152 and the particular target graph curve 904, 906. For example, the orthopaedic surgeon may perform one or more tension balancing surgical procedures to reduce the error between the graph curve 902 and target graph curve 904.

Figure 10:
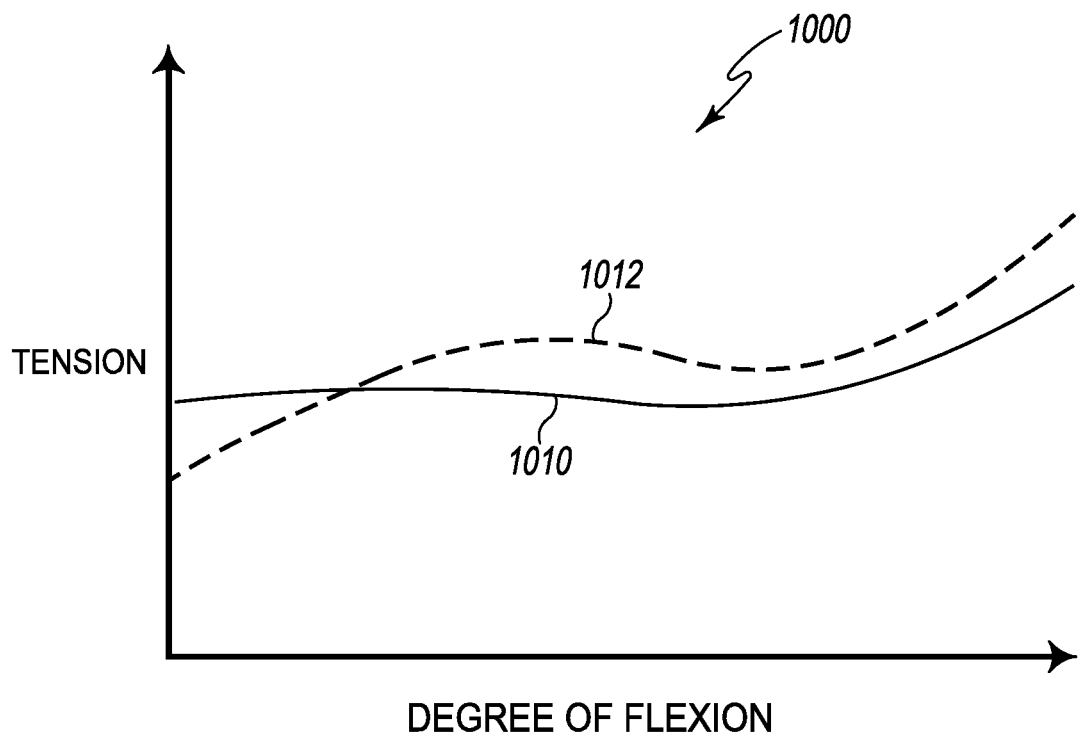
FIG. 10 is another tension-versus-flexion graph illustrating an illustrative pre-operative tension of a medial collateral ligament and a lateral collateral ligament of the patient's knee joint across a range of degrees of flexion.

Additionally or alternatively, in block 716A, the ligament tension analysis device 110 may display a tension-versus-flexion graph for both of the medial or lateral collateral ligaments 150, 152. For example, as shown in FIG. 10, the ligament tension analysis device 110 may generate and display a tension-versus-flexion graph 1000 that includes a graph curve 1010 illustrating the tension data (e.g., measured conductance values or values (quantized values) determined based on the measured conductance) for the medial collateral ligament 150 across the range of degrees of flexion and a graph curve 1012 illustrating the tension data (e.g., measured conductance values or values (quantized values) determined based on the measured conductance) for the lateral collateral ligament 152 across the range of degrees of flexion. As such, as discussed in more detail below, the orthopedic surgeon may utilize the tension-versus-flexion graph 1000 to balance the tension between the medial collateral ligament 150 and the lateral collateral ligament 152. To do so, the orthopaedic surgeon may reduce error between the two graph curves 1010, 1012. For example, the orthopaedic surgeon may perform one or more tension balancing surgical procedures to reduce such that the two graph curves 1010, 1012 better match each other and the error between those graph curve 902 is reduced.

It should be appreciated that, in some embodiments, the steps of blocks 608-616 may be performed using a minimally invasive procedure. In such embodiments, the patient's knee joint 112 may not be exposed in block 604 and minimally invasive ligament couplers 130. For example, the plugs 144 including the needles 400 as shown above in FIG. 4 may be used as minimally invasive ligament couplers and inserted into the corresponding medial collateral ligament 150 or lateral collateral ligament 152 through the patient's skin without exposing the patient's knee joint 112. Such minimally invasive ligament couplers may include shielding or insulation around a portion of the needles 400 to ensure only conductance of the collateral ligaments 150, 152 are measured (and not that of the patient's skin or other soft tissue). The placement of the needles 400 into the that patient's collateral ligaments 150, 152 may be guided, in some embodiments, using appropriate imaging technologies, such as ultrasound.

Regardless, after the orthopaedic surgeon has determined the patient's pre-operative ligament tension for the patient's medial and lateral collateral ligaments 150, 152, the orthopaedic surgeon performs the orthopaedic surgical procedure on the patient's knee joint 102 in block 718. The orthopaedic surgical procedure performed by the orthopaedic surgeon may be embodied as any type of orthopaedic surgical procedure on the patient's knee joint 102 in which the balancing of the tension between the collateral ligaments 150, 152 of the knee joint 102 is desirable. For example, the orthopedic surgical procedure may be embodied as a total knee arthroplasty procedure in which both condyles of the patient's femur and/or tibia are resected and replaced with artificial condyles or a unicompartmental arthroplasty procedure in which only one side of the patient's femur and/or tibia are resected and replaced with artificial condyles.

While performing the orthopaedic surgical procedure, the orthopaedic surgeon may monitor the ligament tension of the collateral ligaments 150, 152 of the knee joint 102 intraoperatively. For example, the orthopaedic surgeon may monitor the tension data 802, 804 displayed on the interface 800, the graph curve 902 of the of the tension-versus-flexion graph 900, and/or the graph curves 1010, 1012 of the tension-versus-flexion graph 1000 while performing the orthopaedic surgical procedure.

Because the orthopaedic surgeon is able to monitor the tension of the medial and lateral collateral ligaments 150, 152 intra-operatively via the ligament tension analysis device 110, the orthopaedic surgeon may also perform balancing of the patent's knee joint 102 intra-operatively in block 722. To do so, in embodiments in which the ligament tension analysis device 110 is incorporated into a ligament balancer, such as the ligament balancer 600 of FIG. 6, the orthopaedic surgeon may operate the ligament balancer 600 to distract the knee joint 102 and facilitate performance of the balancing procedure. As discussed above, in some embodiments, the ligament balancer 600 may be configured to automate a portion of the balancing procedure by distracting the knee joint 102 until the tension data of each of the MCL and LCL are within a threshold value of each other.

Figure 8:
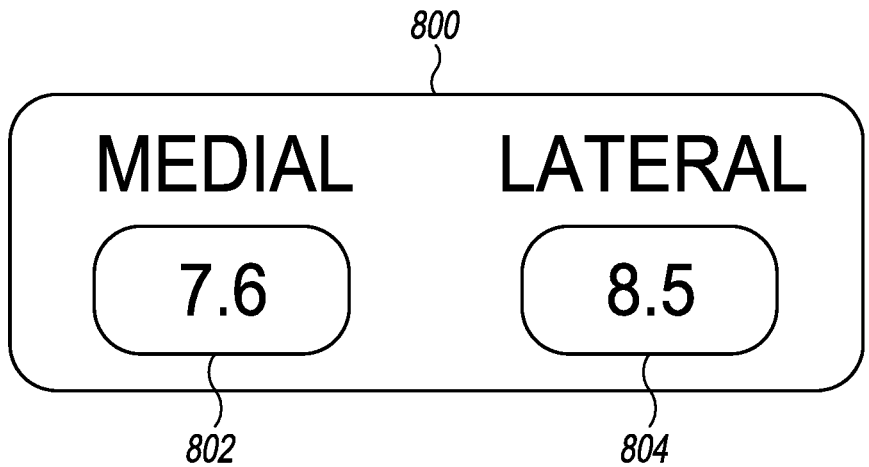
FIG. 8 is an illustration of a display of a ligament tension analysis device of the system of FIG. 1, which is displaying pre-operative conductance values of corresponding ligaments of the patient's knee.
Figure 11:
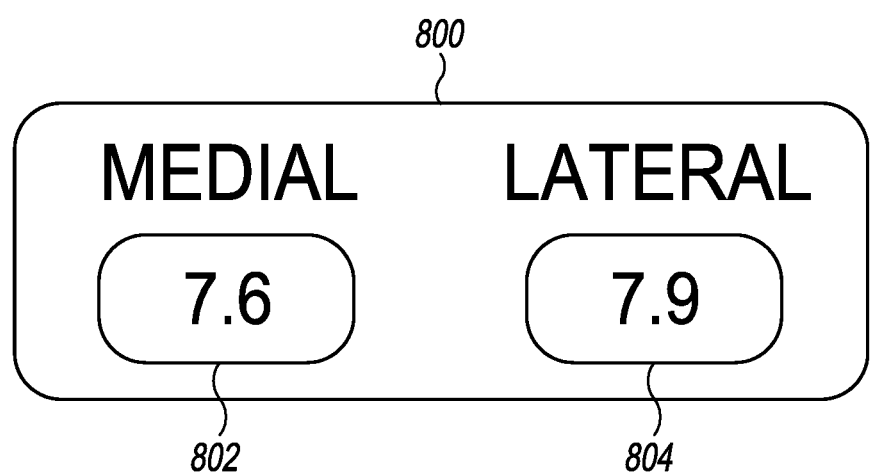
FIG. 11 is another illustration of the display of FIG. 8 displaying intra-operative tension data of corresponding ligaments of the patient's knee during performance of an orthopaedic surgical procedure.
Figure 12:
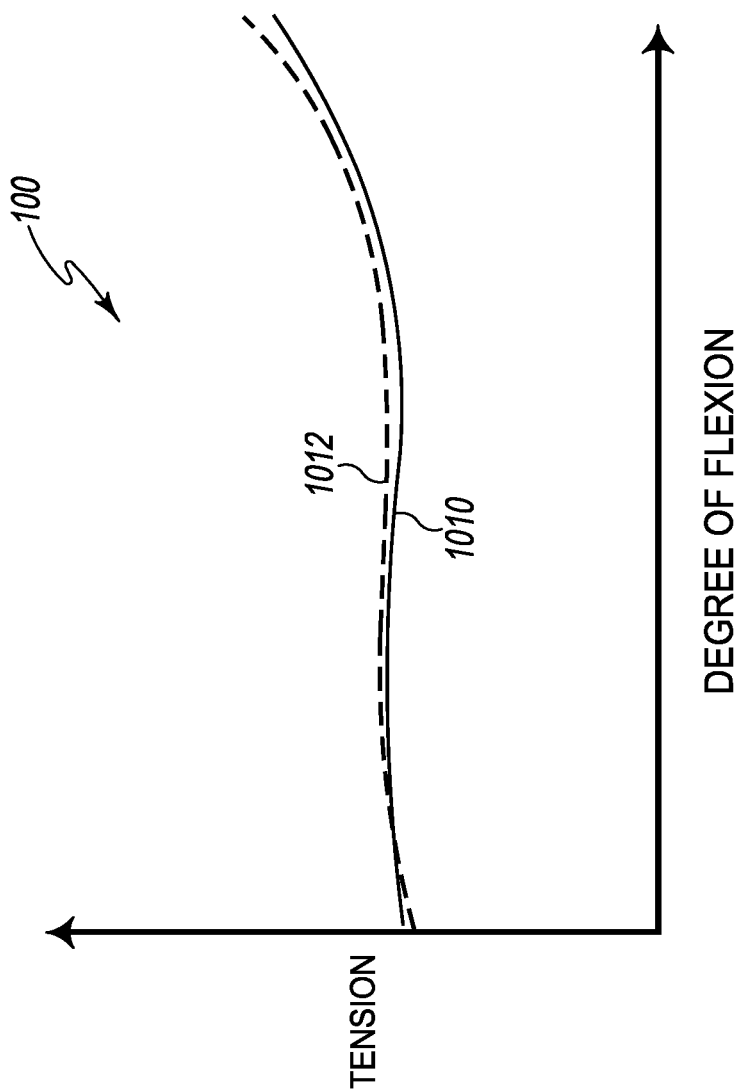
FIG. 12 is a tension-versus-flexion graph illustrating an illustrative post-operative conductance of the medial collateral ligament and the lateral collateral ligament of the patient's knee joint across a range of degrees of flexion.

In block 724, the orthopaedic surgeon may balance the patient's knee by performing a surgical procedure (e.g., bone resection, etc.) to reduce the difference between the tension data 802 of the medial collateral ligament 150 and the tension data 804 of the lateral collateral ligament 152, which are displayed in the interface 800 as shown in FIG. 8. An illustrative example of the tension data 802, 804 (e.g., measured or calculated conductance values) after the orthopedic surgeon has performed a balancing procedure on the patient's knee joint 102 is shown in FIG. 11. As shown in that example, the medial tension 802 has remained relatively constant, but the lateral tension 804 has been lowered such that the difference between the tension data 802, 804 is reduced. In this way, because the tension data 802, 804 (e.g., the measured conductance values or values determined based thereon) are indicative of ligament tension, the tension of the collateral ligaments 150, 152 have been balanced (i.e., are closer in value than they were pre-operatively).

Additionally or alternatively, in block 726, the orthopaedic surgeon may balance the patient's knee joint 112 by performing a surgical procedure (e.g., bone resection, etc.) to reduce the error between the graph curve 1010 of the tension data of the medial collateral ligament 150 over the range of degrees of flexion and the graph curve 1012 of the tension data of the lateral collateral ligament 152 over the range of degrees of flexion, which are shown on the tension-versus-flexion graph 1000. An illustrative example of the graph curves 1010, 1012 after the orthopedic surgeon has performed a balancing procedure on the patient's knee joint 102 is shown in FIG. 13. As shown in that example, the graph curves 1010, 1012 match each other better over the range of degrees of flexion relative to the pre-operative graph curves 1010, 1012 shown in the FIG. 10. Again, because the graph curves 1010, 1012 represent the tension data (e.g., the measured conductance values or values determined based thereon) of the collateral ligaments 150, 152, respectively, over the range of degrees of flexion and the tension data is indicative of ligament tension, the tension of the collateral ligaments 150, 152 has been balanced over the range of degrees of flexion (i.e., are closer in value than they were pre-operatively).

After the orthopaedic surgeon has performed the surgical procedure in block 718, the surgeon may perform any final balancing of the patient's knee joint 112 in block 728. For example, in some embodiments, the orthopaedic surgeon may perform additional bone resectioning or smoothing and/or a ligament release (of ligaments other than medial and lateral collateral ligaments 150, 152) in block 630 to further reduce the difference between the tension data 802, 804. Additionally or alternatively, in block 632, the orthopaedic surgeon may perform additional bone resectioning or smoothing and/or a ligament release (of ligaments other than medial and lateral collateral ligaments 150, 152) to further reduce the error between the graph curve 1010 of the tension data of the medial collateral ligament over the range of degrees of flexion and the graph curve 1012 of the tension data of the lateral collateral ligament over the range of degrees of flexion. In embodiments in which the ligament tension analysis device 110 is incorporated into the ligament balancer 600 of FIG. 6, the orthopaedic surgeon may operate the ligament balancer 600 to distract the knee joint 102 and facilitate performance of the balancing procedure.

Figure 13:
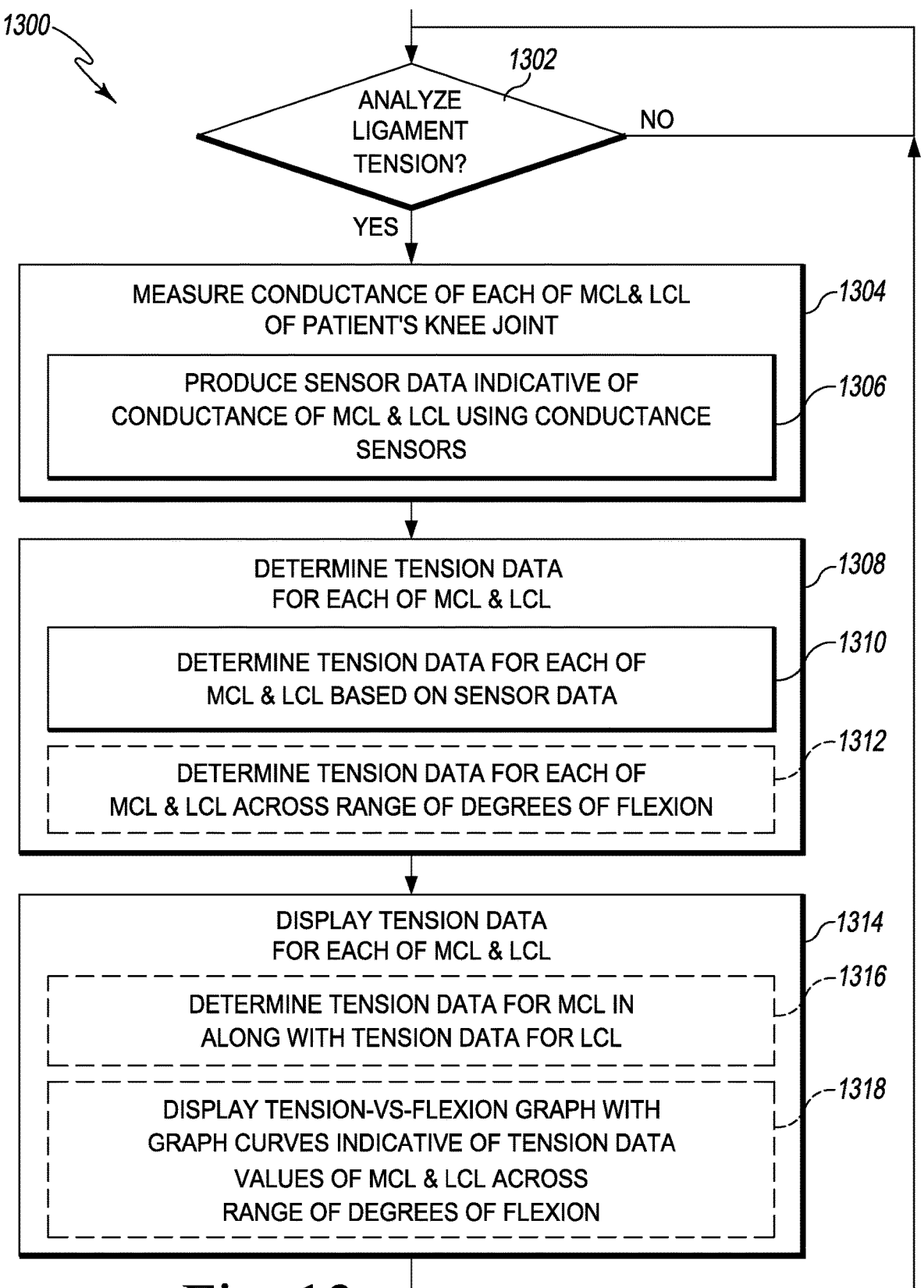
FIG. 13 is simplified flow diagram of an embodiment of a method for determining ligament tension of a knee joint of a patient, which may be executed by the ligament tension analysis device of FIG. 1.

Referring now to FIG. 13, as discussed above, the orthopaedic surgeon may operate the ligament tension analysis device 110 to measure the present conductance of the collateral ligaments 150, 152 of the patient's knee joint 102. To do so, the ligament tension analysis device 110 may execute a method 1300 for determining ligament tension of a knee joint of the patient. The method 1300 begins with block 1302 in which the ligament tension analysis device 110 determines whether the orthopaedic surgeon desires to measure the tension of one or more ligaments. For example, the ligament tension analysis device 110 may await a suitable input from the orthopaedic surgeon before initiating the measurements. If so, the method 1300 advances to block 1304.

In block 1304, the ligament tension analysis device 110 measures the conductance of each of the medial collateral ligament 150 and the lateral collateral ligament 152. In doing so, in block 1306, each of the conductance sensors 120, 122 produce sensor data indicative of the electrical conductance of the collateral ligaments 150, 152. It should be appreciated that the ligament tension analysis device 110 may utilize any suitable technology and/or methodology to measure the conductance of the collateral ligaments 150, 152 depending on the particular conductance sensors 120, 122. For example, as discussed above, the ligament tension analysis device 110 may configured to generate a five (5V) voltage across outputs of each sensor 120, 122 and measure the resulting current. The measured current may then be used to determine a measured resistance according to Ohm's law and the resulting conductance can be determined as the reciprocal of the measured resistance (or determined directly from the measured current). Of course, in other embodiments, analysis signals of different voltages and/or current may be used to measure the conductance of the ligaments to the collateral ligaments 150, 152.

In block 1308, the ligament tension analysis device 110 determines tension data for each of the medial and lateral collateral ligaments 150, 152. To do so, in block 1310, the ligament tension analysis device 110 determines the tension data based on the sensor data produced by the conductance sensors 120, 122. As discussed above, the tension data may be embodied as the raw conductance measurement values (e.g., measured in siemens) or embodied as other numerical values based on the conductance. For example, in some embodiments, the tension data may be embodied as numerical values determined based on a quantization of the measured conductance or based on an output of a mathematical algorithm to which the measured conductance value is an input. Regardless, the determined tension data is indicative of the measured conductance of the collateral ligaments 150, 152, which is itself indicative of the tension of the collateral ligaments 150, 152 as discussed above.

In some embodiments, the ligament tension analysis device 110 may determine the tension data for the collateral ligaments 150, 152 over a range of degrees of flexion in block 1312. To do so, the ligament tension analysis device 110 may use the conductance sensors 120, 122 to determine the relative conductance of the ligaments 150, 152 and use the flexion sensor 128 (or other sensor/device) to determine the present degree of flexion of the patient's knee joint 112 and associate those two measurements to produce an associated graph curve as discussed above. In some embodiments, the orthopaedic surgeon may manually move the patient's knee joint 112 through the desired range of degrees of flexion while the ligament tension analysis device 110 performs the conductance measurements.

Subsequently, in block 1314, the ligament tension analysis device 110 displays the determined tension data for the medial and lateral collateral ligaments 150, 152. For example, in block 1316, the ligament tension analysis device 110 may display the tension data on the display 124 as the conductance values 802, 804 as shown and discussed above in regard to FIG. 8. Additionally or alternatively, in block 1318, the ligament tension analysis device 110 may display the tension data as curve graphs 1010, 1012 as discussed above in regard to FIG. 10. Additionally, in some embodiments, the ligament tension analysis device 110 may also display one or more target curve graphs, similar to target curve graphs 905, 906, as discussed above in regard to FIG. 9.

Regardless of the mode of which the tension data is displayed, the orthopaedic surgeon may utilize the displayed tension data to improve the balancing of the medial and lateral collateral ligaments 150, 152 of the patient's knee joint 102 as discussed above. Additionally, although the ligament tension analysis device 110 has been shown and described above in regard to measurements of the collateral ligaments 150, 152, it should be appreciated that the ligament tension analysis device 110 may be utilized by an orthopaedic surgeon to measure tension of other ligaments of a patient to improve the balancing of such ligaments.

While the disclosure has been illustrated and described in detail in the drawings and foregoing description, such an illustration and description is to be considered as illustrative and not restrictive in character, it being understood that only illustrative embodiments have been shown and described and that all changes and modifications that come within the spirit of the disclosure are desired to be protected.

There are a plurality of advantages of the present disclosure arising from the various features of the methods, apparatuses, and systems described herein. It will be noted that alternative embodiments of the methods, apparatuses, and systems of the present disclosure may not include all of the features described yet still benefit from at least some of the advantages of such features. Those of ordinary skill in the art may readily devise their own implementations of the methods, apparatuses, and systems that incorporate one or more of the features of the present invention and fall within the spirit and scope of the present disclosure as defined by the appended claims.

The invention claimed is:

1. A method for performing an orthopaedic surgical procedure on a knee joint of a patient, the method comprising:
　operating a ligament tension analysis device to measure a conductance of a medial collateral ligament and a conductance of a lateral collateral ligament of the patient's knee joint;
　determining, using the ligament tension analysis device, first tension data for the medial collateral ligament based on the measured conductance of the medial collateral ligament, wherein the first tension data is indicative of an amount of tension of the medial collateral ligament;
　determining, using the ligament tension analysis device, second tension data for the lateral collateral ligament based on the measured conductance of the lateral collateral ligament, wherein the second tension data is indicative of an amount of tension of the lateral collateral ligament;
　displaying the first and second tension data on a display; and
　balancing the tension of the medial collateral ligament and the tension of the lateral collateral ligament of the patient's knee joint based on the measured conductance of the medial collateral ligament and the measured conductance of the lateral collateral ligament.

2. The method of claim 1, wherein balancing the tension of the medial collateral ligament and the tension of the lateral collateral ligament of the patient's knee joint comprises performing an orthopaedic surgical procedure on the patient's knee joint to reduce a difference between the measured conductance of the medial collateral ligament and the conductance of the lateral collateral ligament.

3. The method of claim 1, wherein balancing the tension of the medial collateral ligament and the tension of the lateral collateral ligament of the patient's knee joint comprises balancing the tension of the medial collateral ligament and the tension of the lateral collateral ligament to reduce a difference between the first tension data and the second tension data.

4. The method of claim 1, wherein balancing the tension of the medial collateral ligament and the tension of the lateral collateral ligament of the patient's knee joint comprises balancing the tension of the medial collateral ligament and the tension of the lateral collateral ligament to reduce a difference between first tension data indicative of an amount of tension of the medial collateral ligament and second tension data indicative of an amount of tension of the lateral collateral ligament, wherein the first tension data is determined based on the measured conductance of the medial collateral ligament and the second tension data is determined based on the measured conductance of the lateral collateral ligament.

5. The method of claim 1, wherein measuring the conductance of the medial collateral ligament and the conductance of a lateral collateral ligament of the patient's knee joint comprises measuring the conductance of the medial collateral ligament and the conductance of a lateral collateral ligament across a range of degrees of flexion of the patient's knee joint.

6. The method of claim 5, wherein measuring the conductance of the medial collateral ligament and the conductance of the lateral collateral ligament of the patient's knee joint comprises operating a ligament tension analysis device to:
　(i) measure the conductance of the medial collateral ligament across the range of degrees of flexion of the patient's knee joint and the conductance of the lateral collateral ligament across the range of degrees of flexion of the patient's knee joint,
　(ii) determine a first set of tension data values for the medial collateral ligament across the range of degrees of flexion of the patient's knee joint based on the measured conductance of the medial collateral ligament, wherein each tension value of the first set of tension data values is indicative of an amount of tension of the medial collateral ligament at a corresponding degree of flexion of the patient's knee joint,
　(iii) determine a second set of tension data values for the lateral collateral ligament across the range of degrees of flexion of the patient's knee joint based on the measured conductance of the lateral collateral ligament, wherein each tension value of the second set of tension data values is indicative of an amount of tension of the lateral collateral ligament at a corresponding degree of flexion of the patient's knee joint, and
　(iv) display a tension-versus-flexion graph having a first graph curve indicative of the first set of tension data values across the range of degrees of flexion of the patient's knee joint and a second graph curve indicative of the second set of tension data values across the range of degrees of flexion of the patient's knee joint.

7. The method of claim 6, wherein balancing the tension of the medial collateral ligament and the tension of the lateral collateral ligament of the patient's knee joint comprises balancing the tension of the medial collateral ligament and the tension of the lateral collateral ligament to reduce an error between the first graph curve and the second graph curve.

8. The method of claim 1, wherein balancing the tension of the medial collateral ligament and the tension of the lateral collateral ligament comprises performing a ligament balancing procedure of the patient's knee joint.

9. The method of claim 8, wherein performing a ligament balancing procedure of the patient's knee joint comprises performing a ligament release procedure.

10. The method of claim 1, wherein balancing the tension of the medial collateral ligament and the tension of the lateral collateral ligament comprises periodically monitoring the measured conductance of the medial collateral ligament and the measured conductance of a lateral collateral ligament of the patient's knee joint while performing an orthopaedic surgical procedure on the patient's knee joint.

11. A method for performing an orthopaedic surgical procedure on a knee joint of a patient, the method comprising:
   measuring a conductance of a medial collateral ligament and a conductance of a lateral collateral ligament of the patient's knee joint, wherein the measured conductance of each collateral ligament is indicative of an amount of tension of the corresponding medial collateral ligament and lateral collateral ligament; and
   balancing the tension of the medial collateral ligament and the tension of the lateral collateral ligament of the patient's knee joint based on the measured conductance of the medial collateral ligament and the measured conductance of the lateral collateral ligament,
   wherein balancing the tension of the medial collateral ligament and the tension of the lateral collateral ligament of the patient's knee joint comprises balancing the tension of the medial collateral ligament and the tension of the lateral collateral ligament to reduce an error between (i) a first tension-versus-flexion graph curve indicative of a first set of tension data values of the medial collateral ligament across a range of degrees of flexion of the patient's knee joint and (ii) a second tension-versus-flexion graph curve indicative of a second set of tension data values of the lateral collateral ligament across the range of degrees of flexion of the patient's knee joint.

12. The method of claim 11, wherein balancing the tension of the medial collateral ligament and the tension of the lateral collateral ligament of the patient's knee joint comprises performing an orthopaedic surgical procedure on the patient's knee joint to reduce a difference between the measured conductance of the medial collateral ligament and the conductance of the lateral collateral ligament.

13. The method of claim 11, wherein measuring the conductance of the medial collateral ligament and the conductance of a lateral collateral ligament of the patient's knee joint comprises measuring the conductance of the medial collateral ligament and the conductance of a lateral collateral ligament across a range of degrees of flexion of the patient's knee joint.

14. The method of claim 11, wherein balancing the tension of the medial collateral ligament and the tension of the lateral collateral ligament comprises performing a ligament balancing procedure of the patient's knee joint.

15. A method for performing an orthopaedic surgical procedure on a knee joint of a patient, the method comprising:
   coupling a first ligament coupler to the medial collateral ligament by encircling the medial collateral ligament with the first ligament coupler;
   coupling a second ligament coupler to the lateral collateral ligament by encircling the lateral collateral ligament with the second ligament coupler;
   measuring a conductance of a medial collateral ligament and a conductance of a lateral collateral ligament of the patient's knee joint using the first and second ligament couplers, wherein the measured conductance of each collateral ligament is indicative of an amount of tension of the corresponding medial collateral ligament and lateral collateral ligament; and
   balancing the tension of the medial collateral ligament and the tension of the lateral collateral ligament of the patient's knee joint based on the measured conductance of the medial collateral ligament and the measured conductance of the lateral collateral ligament.

16. The method of claim 15, wherein balancing the tension of the medial collateral ligament and the tension of the lateral collateral ligament of the patient's knee joint comprises performing an orthopaedic surgical procedure on the patient's knee joint to reduce a difference between the measured conductance of the medial collateral ligament and the conductance of the lateral collateral ligament.

17. The method of claim 15, wherein measuring the conductance of the medial collateral ligament and the conductance of a lateral collateral ligament of the patient's knee joint comprises measuring the conductance of the medial collateral ligament and the conductance of a lateral collateral ligament across a range of degrees of flexion of the patient's knee joint.

18. The method of claim 15, wherein balancing the tension of the medial collateral ligament and the tension of the lateral collateral ligament comprises performing a ligament balancing procedure of the patient's knee joint.

* * * * *